(12) United States Patent
Matta et al.

(10) Patent No.: US 9,604,968 B2
(45) Date of Patent: Mar. 28, 2017

(54) PURE CRYSTALLINE FORM II OF L-MALIC ACID SALT OF SUNITINIB AND PROCESSES FOR ITS PREPARATION

(71) Applicant: RANBAXY LABORATORIES LIMITED, New Delhi, Delhi (IN)

(72) Inventors: Hari Babu Matta, Prakasam (IN); Mahavir Singh Khanna, New Delhi (IN); Mohan Prasad, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 200 days.

(21) Appl. No.: 14/147,757

(22) Filed: Jan. 6, 2014

(65) Prior Publication Data

US 2015/0112085 A1  Apr. 23, 2015

(30) Foreign Application Priority Data

Oct. 18, 2013  (IN) .......................... 3112/DEL/2013

(51) Int. Cl.
*C07D 403/06* (2006.01)
*C07C 59/245* (2006.01)

(52) U.S. Cl.
CPC .......... *C07D 403/06* (2013.01); *C07C 59/245* (2013.01)

(58) Field of Classification Search
None
See application file for complete search history.

(56) References Cited

U.S. PATENT DOCUMENTS

| | | | | |
|---|---|---|---|---|
| 6,573,293 | B2 | 6/2003 | Tang et al. | 514/414 |
| 7,125,905 | B2 | 10/2006 | Tang et al. | 514/414 |
| 2003/0069298 | A1 | 4/2003 | Hawley et al. | 514/414 |
| 2007/0191458 | A1 | 8/2007 | Hawley et al. | 514/414 |

FOREIGN PATENT DOCUMENTS

| | | | |
|---|---|---|---|
| CN | 103833733 | 6/2014 | ........... C07D 403/06 |
| WO | WO 03/016305 | 2/2003 | ........... C07D 403/06 |
| WO | WO 2009/067686 | 5/2009 | ........... C07D 403/06 |
| WO | WO 2009/104021 | 8/2009 | ........... C07D 403/06 |
| WO | WO 2009/156837 | 12/2009 | ........... C07D 403/06 |
| WO | WO 2010/004339 | 1/2010 | ........... C07D 403/06 |
| WO | WO 2010/010454 | 1/2010 | ........... C07D 403/06 |
| WO | WO 2010/011834 | 1/2010 | ........... C07D 403/06 |
| WO | WO 2010/041134 | 4/2010 | ........... C07D 403/06 |
| WO | WO 2010/055082 | 5/2010 | ........... C07D 403/06 |
| WO | WO 2010/076805 | 7/2010 | ........... C07D 403/06 |
| WO | WO 2011/058521 | 5/2011 | ........... C07D 403/06 |
| WO | WO 2011/061613 | 5/2011 | ........... C07D 403/06 |
| WO | WO 2011/092664 | 8/2011 | ........... C07D 403/06 |
| WO | WO 2012/058780 | 5/2012 | ........... C07D 403/06 |
| WO | WO 2012/059941 | 5/2012 | ........... C07D 403/06 |

OTHER PUBLICATIONS

Sidoryk et al., "Physicochemical Characteristics of Sunitinib Malate and its Process-Related Impurities", *Journal of Pharmaceutical Sciences*, 102(2):706-716 (2013).

*Primary Examiner* — Alicia L Otton

(57) ABSTRACT

The present invention relates to pure crystalline Form II of an L-malic acid salt of sunitinib and a process for its preparation. The invention further provides crystalline Form II of an L-malic acid salt of sunitinib having a purity of at least 97.0%. The invention also provides crystalline Form II of an L-malic acid salt of sunitinib substantially free of an anti-oxidant. The invention also provides crystalline Form II of L-malic acid salt of sunitinib which remains chemically pure on storage at 25° C.±2° C. and 40° C.±2° C. at a relative humidity of 60%±5% and 75%±5%, respectively, for at least 1 month.

20 Claims, 6 Drawing Sheets

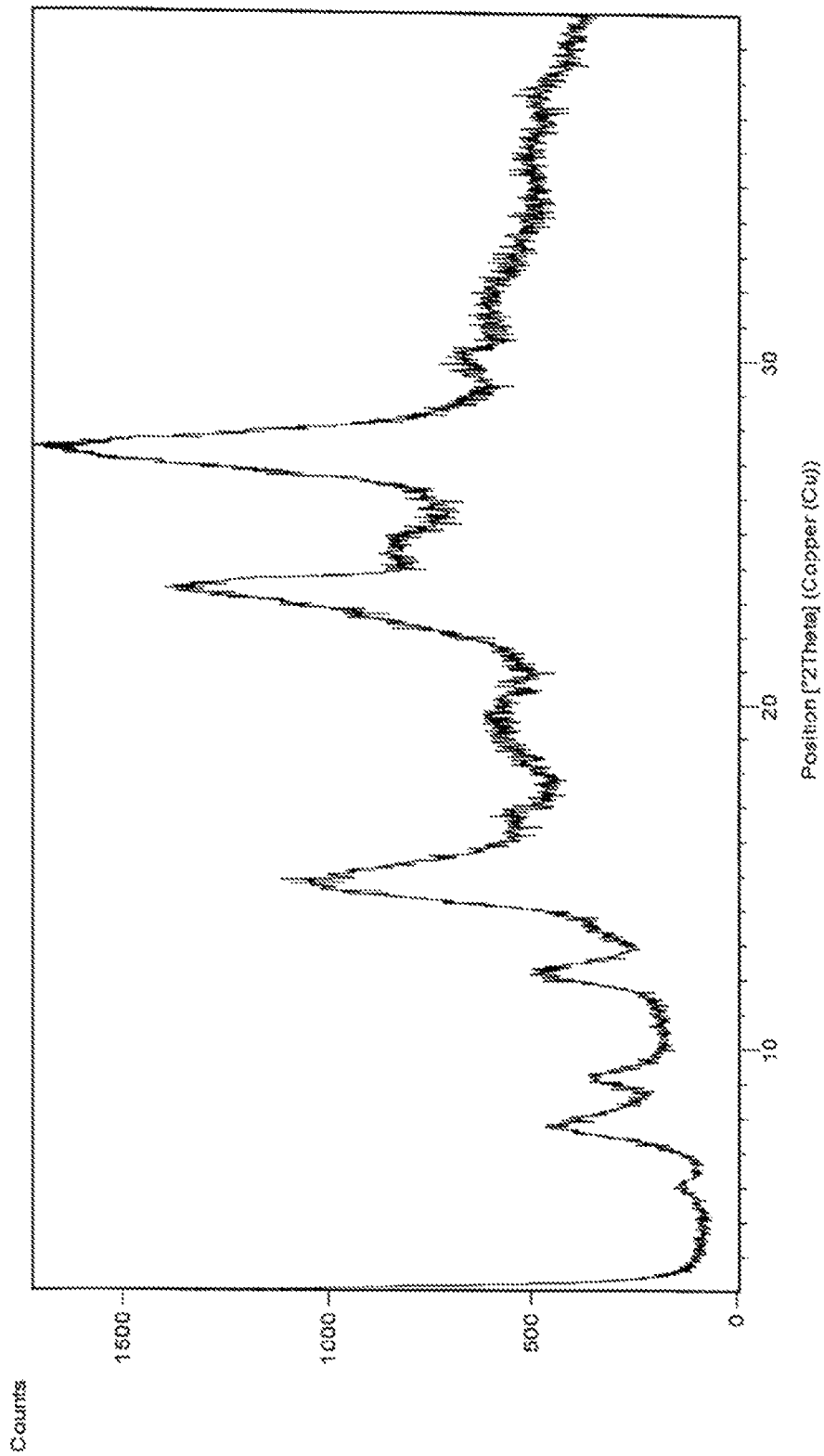
FIGURE 1: XRPD PATTERN OF THE PURE CRYSTALLINE FORM II OF L-MALIC ACID SALT OF SUNITINIB PREPARED ACCORDING TO EXAMPLE 4.

Figure 1A: Table of values for the XRPD pattern depicted in Figure 1.

| Pos [°2Th] | d-spacing [Å] | Rel. Int. [%] |
|---|---|---|
| 3.08 | 28.64 | 89.12 |
| 6.09 | 14.52 | 3.65 |
| 7.72 | 11.45 | 31.26 |
| 9.15 | 9.67 | 19.93 |
| 12.09 | 7.32 | 22.06 |
| 14.77 | 6.00 | 61.54 |
| 23.54 | 3.78 | 54.00 |
| 27.38 | 3.26 | 100.00 |
| 30.11 | 2.97 | 7.28 |
| 37.71 | 2.38 | 4.15 |

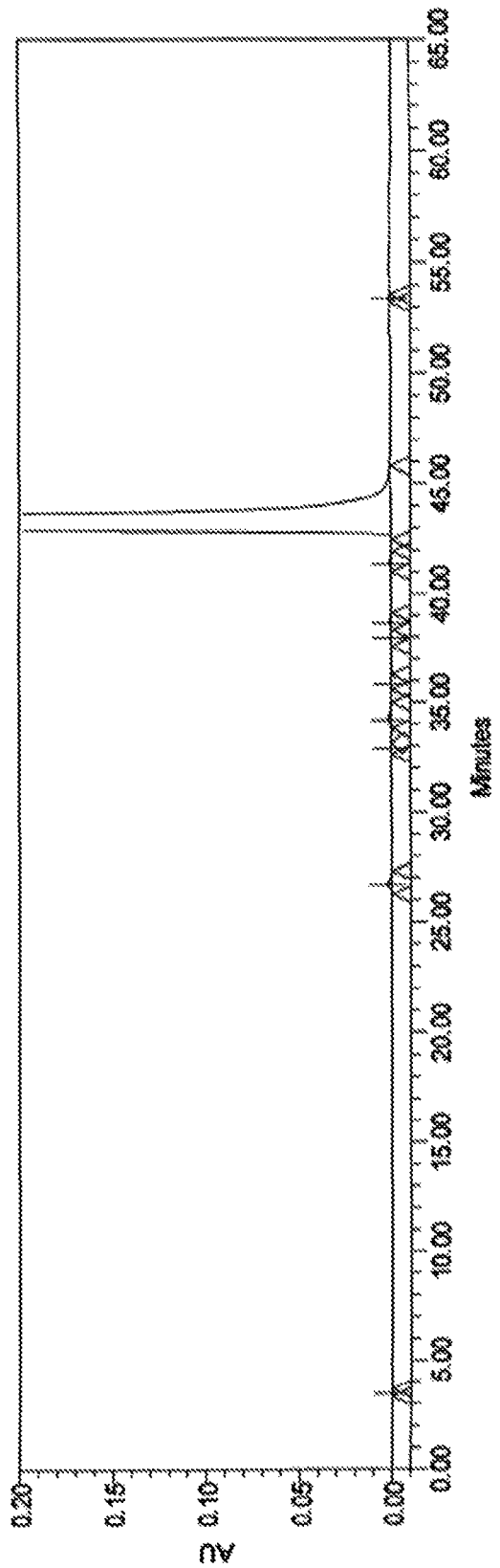
FIGURE 2: HIGH-PERFORMANCE LIQUID CHROMATOGRAM (HPLC) OF PURE FORM II OF SUNITINIB MALATE PREPARED ACCORDING TO EXAMPLE 4.

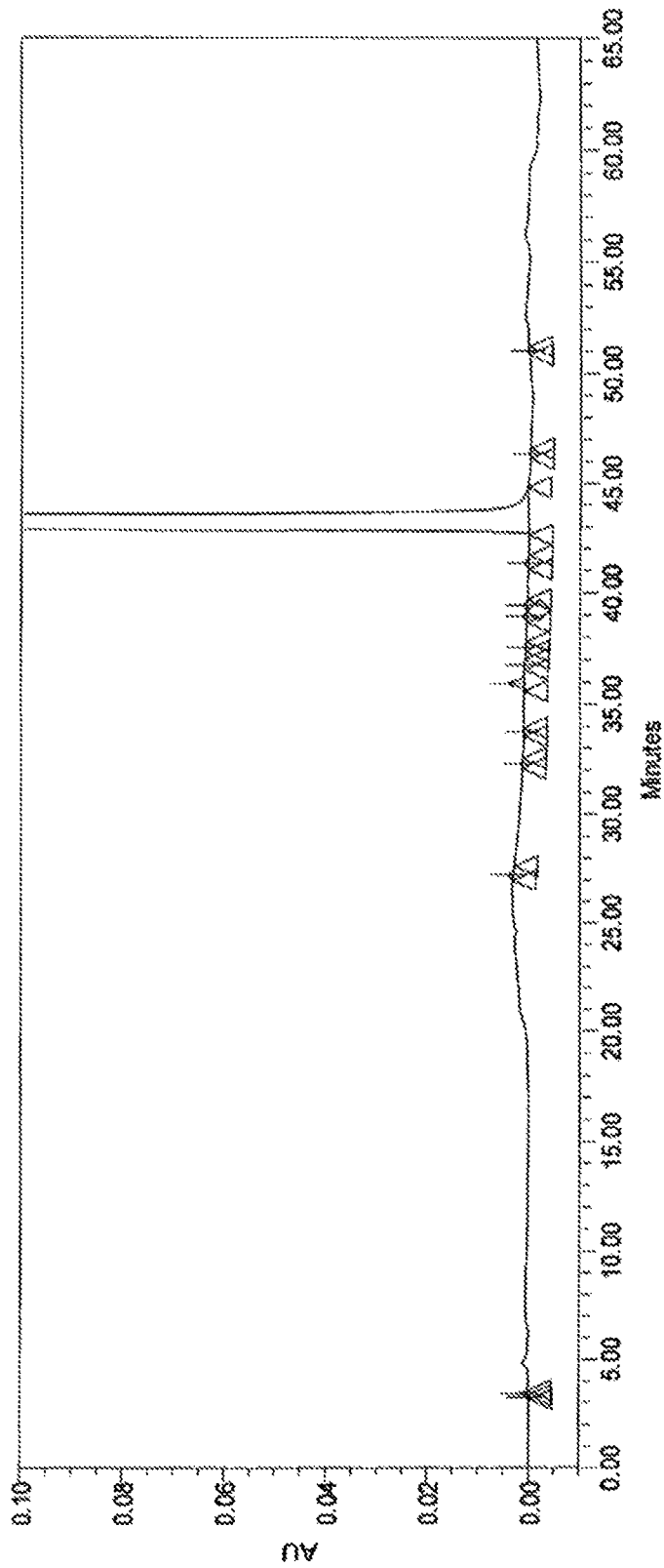
FIGURE 3: HPLC OF PURE FORM II OF SUNITINIB MALATE PREPARED ACCORDING TO EXAMPLE 4 AFTER 1 MONTH STORAGE AT 25°C ±2°C AT A RELATIVE HUMIDITY OF 60% ±5%.

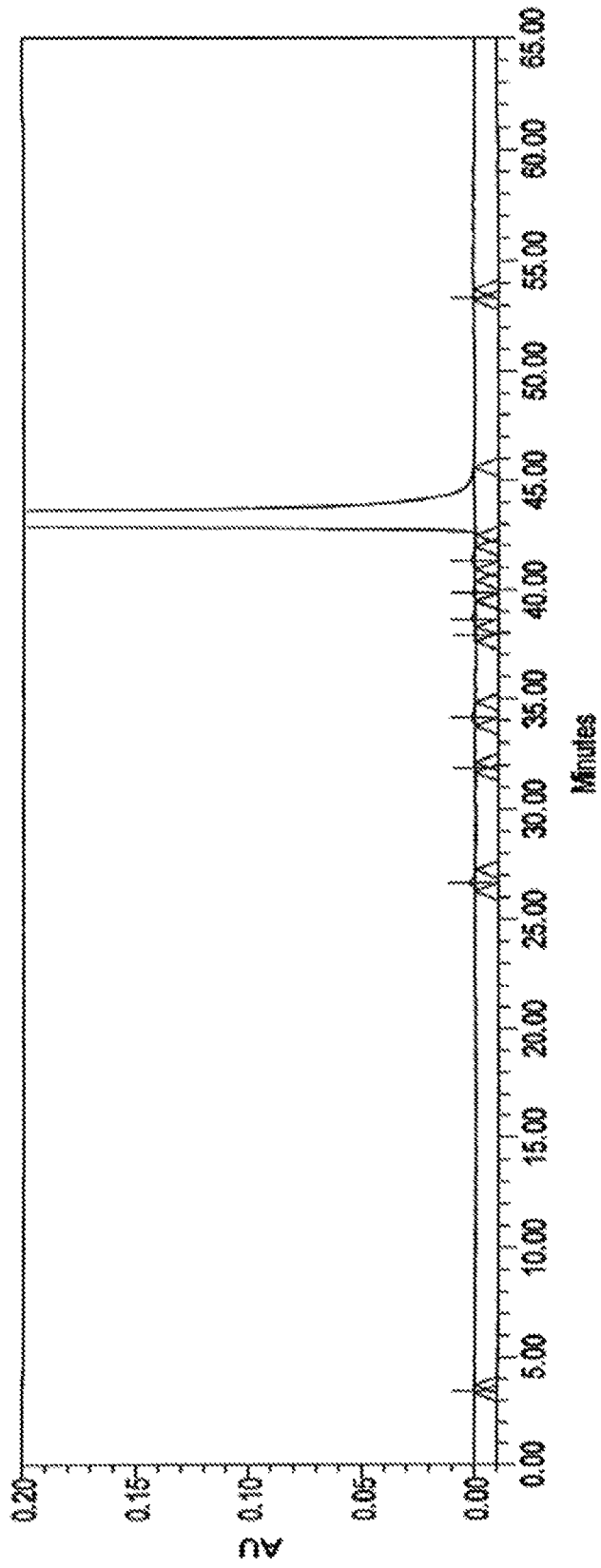
FIGURE 4: HPLC OF FORM II OF SUNITINIB MALATE PREPARED ACCORDING TO EXAMPLE 7.

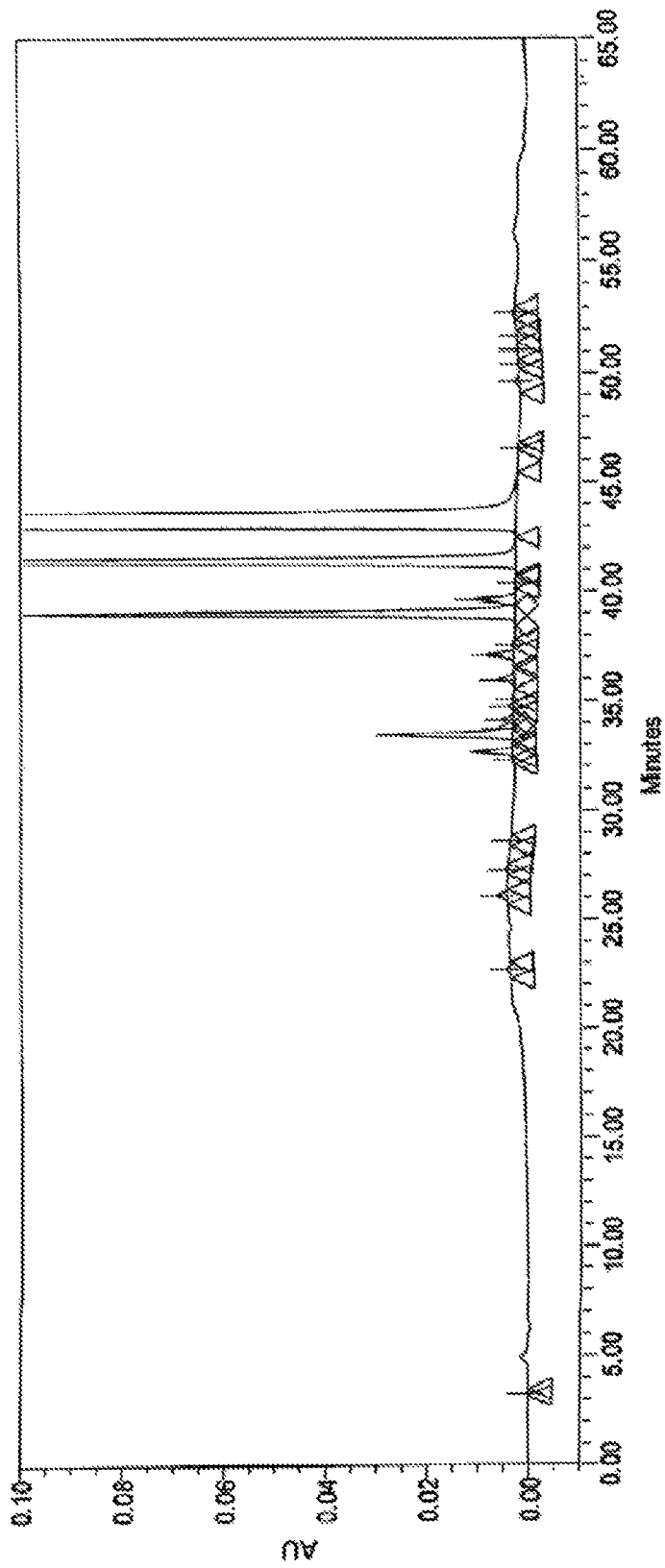
FIGURE 5: HPLC OF PURE FORM II OF SUNITINIB MALATE PREPARED ACCORDING TO EXAMPLE 7 AFTER 1 MONTH STORAGE AT 25°C ±2°C AT A RELATIVE HUMIDITY OF 60% ±5%.

PURE CRYSTALLINE FORM II OF L-MALIC ACID SALT OF SUNITINIB AND PROCESSES FOR ITS PREPARATION

FIELD OF THE INVENTION

The present invention relates to pure crystalline Form II of an L-malic acid salt of sunitinib and a process for its preparation. The invention further provides crystalline Form II of an L-malic acid salt of sunitinib having a purity of at least 97.0%. The invention also provides crystalline Form II of an L-malic acid salt of sunitinib substantially free of an anti-oxidant. The invention also provides crystalline Form II of an L-malic acid salt of sunitinib which remains chemically pure on storage at 25° C.±2° C. and 40° C.±2° C. at a relative humidity of 60%±5% and 75%±5%, respectively, for at least 1 month.

BACKGROUND OF THE INVENTION

Sunitinib is chemically described as N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide and is represented by Formula I.

FORMULA I

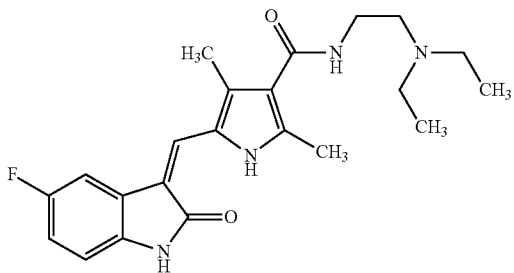

Sunitinib is an oral multi-kinase inhibitor and is useful for the treatment of gastrointestinal stromal tumors and advanced renal cell carcinoma. Sunitinib is commercially available as an L-malate salt, which is described chemically as butanedioic acid, hydroxy-, (2S)-, compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1).

U.S. Publication Nos. 2003/0069298 and 2007/0191458 describe the preparation of crystal Forms I and II of an L-malic acid salt of sunitinib. According to these publications, crystal Form I of an L-malic acid salt of sunitinib is prepared by a process comprising slurrying a poorly crystalline or crystal Form II of an L-malic acid salt of sunitinib in acetonitrile, and crystal Form II of an L-malic acid salt of sunitinib is prepared by dissolving crystal Form I of an L-malic acid salt of sunitinib in tetrahydrofuran and water and allowing the solvent to evaporate overnight. PCT Publication No. WO 2009/104021 discloses that Form II of sunitinib L-malate is hygroscopic, thermodynamically unstable, and appears to readily convert to Form I.

PCT Publication No. WO 2011/061613 discloses a stable crystalline Form II of an L-malic acid salt of sunitinib and a process for its preparation. The publication further describes that the stable crystalline Form II does not convert to any other form or absorb moisture on storage.

SUMMARY OF THE INVENTION

The present invention provides another stable crystalline Form II of an L-malic acid salt of sunitinib which remains stable in terms of purity, as well as polymorphic form consistency, and does not absorb moisture over time. Both chromatographic and polymorphic stability are achieved by the methods of the present invention. The invention further provides crystalline Form II of an L-malic acid salt of sunitinib with a purity of at least 97.0%. The invention also provides crystalline Form II of an L-malic acid salt of sunitinib substantially free of an anti-oxidant.

DETAILED DESCRIPTION OF THE INVENTION

The term "L-malic acid salt of sunitinib", as used herein, includes a combination of sunitinib and L-malic acid in any ratio from about 1:0.75 to about 1:1.5.

The term "charging", as used herein, includes mixing, loading, filling, introducing, pouring, infusing, and/or adding.

The term "about", as used herein, refers to any value which lies within the range defined by a variation of up to ±10% of the value.

The term "substantially free of an anti-oxidant", as used herein, refers to a content of an anti-oxidant which is less than or equal to 2.0%.

The term "substantially free of an impurity at relative retention time (RRT) of 0.96", as used herein, refers to a content of an anti-oxidant in pure Form II of an L-malic acid salt of sunitinib which is less than or equal to 0.5%.

A first aspect of the present invention provides a pure crystalline Form II of an L-malic acid salt of sunitinib.

In an embodiment of the first aspect, the pure crystalline Form II of the L-malic acid salt of sunitinib has a purity of not less than 97.0% as measured by a chromatographic technique such as High-Performance Liquid Chromatography (HPLC).

In another embodiment, the pure crystalline Form II of the L-malic acid salt is chemically stable and does not degrade on storage at 25° C.±2° C. and 40° C.±2° C. at a relative humidity of 60%±5% and 75%±5%, respectively, for at least 1 month. The pure crystalline Form II of the L-malic acid salt does not absorb moisture on storage.

A second aspect of the present invention provides pure crystalline Form II of an L-malic acid salt of sunitinib having a purity of at least 97.0%.

A third aspect of the present invention provides a process for the preparation of pure crystalline Form II of an L-malic acid salt of sunitinib, wherein the process comprises:
 a) adding an anti-oxidant to a mixture of L-malic acid and sunitinib; and
 b) isolating pure crystalline Form II of the L-malic acid salt of sunitinib from the mixture obtained in step a).

Sunitinib may be prepared by any of the methods known in the literature, such as those described in U.S. Pat. Nos. 7,125,905 and 6,573,293. The sunitinib used in step a) may be in solid form or may be in the form of a solution carried forward from the previous step.

In an embodiment of this aspect, the anti-oxidant used in the preparation of pure Form II of the L-malic acid salt of sunitinib may be organic or inorganic.

Examples of organic anti-oxidants include ascorbic acid, L-ascorbic acid, sodium ascorbate, calcium ascorbate, fatty acid esters of ascorbic acid, vitamins A and E, lipoic acid, uric acid, carotenes, glutathione, melatonin, tocopheroles, propylgallate (PG), octylgallate, dodecylgallate, tertiary butylhydroquinone (TBHQ), butylated hydroxyanisole (BHA), butylated hydroxytoluene (BHT), erythorbic acid, sodium erythorbate, 4-hexylresorcinol, polyphenols, and mixtures thereof. Examples of inorganic anti-oxidants include sodium metabisulfite, sulfur dioxide, sulfites, and mixtures thereof. The preferred organic anti-oxidant is L-ascorbic acid. The preferred inorganic anti-oxidant is sodium metabisulfite.

In another embodiment of this aspect, the addition of an anti-oxidant to a mixture of L-malic acid and sunitinib is carried out in the presence or absence of a solvent. The solvent is selected from the group consisting of water, ethers, alcohols, ketones, hydrocarbons, esters, halogenated hydrocarbons, and mixtures thereof.

Examples of ether solvents include tetrahydrofuran and diethyl ether. Examples of alcohol solvents include methanol, ethanol, and n-butanol. Examples of ketone solvents include acetone and methyl ethyl ketone. Examples of hydrocarbon solvents include pentane, hexane, and heptane. Examples of ester solvents include ethyl acetate, butyl acetate, and isopropyl acetate. An example of a halogenated hydrocarbon is dichloromethane. The preferred solvent is water.

In another embodiment of this aspect, the pure crystalline Form II of the L-malic acid salt of sunitinib is obtained from the reaction mixture of step a) by spray drying, freeze drying, agitated thin film drying, melt extrusion, solvent evaporation, desolvation, ball milling, precipitation, or the like. The preferred method is freeze drying.

The reaction mixture or the solution may optionally be filtered prior to spray drying, freeze drying, agitated thin film drying, melt extrusion, solvent evaporation, desolvation, ball milling, precipitation, or the like. The temperature, feed rate, and vacuum may be adjusted to optimize output and particle size. The temperature of the freeze drier may be controlled from about −70° C. to about −90° C., for example, about −82° C. to about −83° C. After freeze drying, the pure crystalline Form II of the L-malic acid salt of sunitinib is collected (isolated) from the dryer and optionally further dried under vacuum to remove residual solvents. The pure Form II of the L-malic acid salt of sunitinib so obtained is chemically stable and has substantially the same XRPD pattern as depicted in FIG. 1. The obtained pure crystalline Form II of the L-malic acid salt of sunitinib has a purity of not less than 97.0% as measured by a chromatographic technique such as high-performance liquid chromatography (HPLC). The obtained crystalline Form II of the L-malic acid salt of sunitinib is characterized by its consistent purity. In the context of the present invention, the consistency in purity of the crystalline Form II refers to the purity wherein the changes in purity over the time will not be more than 2%.

Table 1 below compares the chromatographic purity of crystalline Form II of an L-malic acid salt of sunitinib prepared without using an anti-oxidant (as per Example 8), and pure crystalline Form II of an L-malic acid salt of sunitinib prepared using an anti-oxidant (as per Examples 1, 2, and 4), on storage at 25° C.±2° C. and 40° C.±2° C. at a relative humidity of 60%±5% and 75%±5%, respectively, for 1 month and above.

TABLE 1

| Example No. | Chromatographic Purity (Initial) | Chromatographic Purity (1M storage at 25° C. ± 2° C./ 60% ± 5% RH) | Chromatographic Purity (1M storage at 40° C. ± 2° C./ 75% ± 5% RH) |
|---|---|---|---|
| Example 1 (with 0.02% sodium metabisulfite) | 99.1% w/w | 98.4% w/w | 97.0% w/w |
| Example 2 (with 0.05% sodium metabisulfite) | 99.7% w/w | 98.7% w/w | 97.3% w/w |
| Example 4 (with 0.01% ascorbic acid) | 99.7% w/w | 99.7% w/w | 99.3% w/w |
| Example 8 (without anti-oxidant) | 99.5% w/w | 87.4% w/w | 87.8% w/w |

Table 1 represents the effect of using an anti-oxidant on the purity of crystalline Form II of an L-malic acid salt of sunitinib. The use of an anti-oxidant during the manufacturing process effectively stabilizes the purity of crystalline Form II of an L-malic acid salt of sunitinib.

A fourth aspect of the present invention provides a process for the preparation of pure crystalline Form II of an L-malic acid salt of sunitinib, wherein the process comprises:
  a) adding sunitinib ascorbate to a mixture of L-malic acid and sunitinib; and
  b) isolating pure crystalline Form II of the L-malic acid salt of sunitinib from the reaction mixture obtained in step a).

A fifth aspect of the present invention provides a process for the preparation of pure crystalline Form II of an L-malic acid salt of sunitinib, wherein the process comprises:
  a) reacting sunitinib ascorbate with L-malic acid; and
  b) isolating pure crystalline Form II of the L-malic acid salt of sunitinib from the reaction mixture thereof.

A sixth aspect of the present invention provides a pure crystalline Form II of an L-malic acid salt of sunitinib substantially free of an anti-oxidant.

The pure crystalline Form II of an L-malic acid salt of sunitinib substantially free of an anti-oxidant herein refers to the Form II having an anti-oxidant content of less than 2.0%, preferably less than 1.0%, and more preferably less than 0.5%.

A seventh aspect of the present invention provides a pure crystalline Form II of an L-malic acid salt of sunitinib substantially free of ascorbic acid.

In one embodiment of this aspect, the pure crystalline Form II of the L-malic acid salt of sunitinib has an ascorbic acid content of less than 2.0%, preferably less than 1%, and more preferably less than 0.5%.

An eighth aspect of the present invention provides a pure crystalline Form II of an L-malic acid salt of sunitinib substantially free of an impurity at relative retention time (RRT) of 0.96 as measured by high-performance liquid chromatography (HPLC).

In an embodiment of this aspect, the content of the impurity at RRT of 0.96 is less than 0.5%, preferably less than 0.1%. The impurity at RRT of 0.96 can be chemically characterized by Mass Spectroscopy (MS) and Nuclear Magnetic Resonance (NMR). The content of the impurity at RRT of 0.96, in pure Form II prepared by the process that uses an anti-oxidant, remains stable on 1 month storage at 25° C.±2° C. at a relative humidity of 60%±5% as depicted in FIGS. 3 and 4. The content of impurity at RRT of 0.96, in Form II of sunitinib malate prepared by the process that does not make use of an anti-oxidant, increases on 1 month storage at 25° C.±2° C. at a relative humidity of 60%±5% as depicted in FIGS. 5 and 6.

BRIEF DESCRIPTION OF THE DRAWINGS

FIG. 1 depicts the X-Ray Powder Diffractometer (XRPD) pattern of the pure crystalline Form II of an L-malic acid salt of sunitinib prepared according to Example 4.

FIG. 1A provides the table of values for the XRPD pattern depicted in FIG. 1.

FIG. 2 depicts the High-Performance Liquid Chromatogram (HPLC) of pure Form II of an L-malic acid salt of sunitinib prepared according to Example 4.

FIG. 3 depicts the HPLC of pure Form II of an L-malic acid salt of sunitinib prepared according to Example 4 after 1 month storage at 25° C.±2° C. at a relative humidity of 60%±5%.

FIG. 4 depicts the HPLC of Form II of an L-malic acid salt of sunitinib prepared according to Example 7.

FIG. 5 depicts the HPLC of pure Form II of an L-malic acid salt of sunitinib prepared according to Example 7 after 1 month storage at 25° C.±2° C. at a relative humidity of 60%±5%.

The XRPD of the samples were determined by using PANalytical® X'Pert Pro X-Ray Powder Diffractometer in the range 3-40 degree 2 theta and under tube voltage and current of 45 Kv and 40 mA, respectively. Copper radiation of wavelength 1.54 angstrom and X'Celerator® detector was used.

While the present invention has been described in terms of its specific embodiments, certain modifications and equivalents will be apparent to those skilled in the art and are intended to be included within the scope of the present invention.

EXAMPLES

Example 1

Preparation of Pure Crystalline Form II of L-Malic Acid Salt of Sunitinib

Sunitinib (25 g), L-malic acid (8.41 g), and sodium metabisulfite (0.05 g; 0.02%) were added to de-ionized water (437.5 mL) at 35° C. to 40° C. for 1 hour. The solution was filtered and added to a freeze dryer for 48 hours. The following parameters were controlled in the freeze drying process:
Freeze dryer: Telstar® LyoQuest
Temperature: −82.3° C.
Vacuum: 0.036 mbar
Weight: 24.2 g
Chromatographic Purity (Initial): 99.10%
Chromatographic Purity after 1M storage (at 40° C.±2° C./75%±5% RH): 97.0%
Chromatographic Purity after 1M storage (at 25° C.±2° C./60%±5% RH): 98.4%

Example 2

Preparation of Pure Crystalline Form II of L-Malic Acid Salt of Sunitinib

Sunitinib (25 g), L-malic acid (8.41 g), and sodium metabisulfite (0.125 g; 0.05%) were added to de-ionized water (437.5 mL) at 35° C. to 40° C. for 1 hour. The solution was filtered and added to a freeze dryer for 48 hours. The following parameters were controlled in the freeze drying process:
Freeze dryer: Telstar® LyoQuest
Temperature: −82.3° C.
Vacuum: 0.036 mbar
Weight: 23.9 g
Chromatographic Purity (Initial): 99.70%
Chromatographic Purity after 1M storage (at 40° C.±2° C./75%±5% RH): 97.3%
Chromatographic Purity after 1M storage (at 25° C.±2° C./60%±5% RH): 98.7%

Example 3

Preparation of Pure Crystalline Form II of L-Malic Acid Salt of Sunitinib

Sunitinib (20 g), L-malic acid (6.73 g), and sodium metabisulfite (0.2 g; 0.1%) were added to de-ionized water (350 mL) at 35° C. to 40° C. for 1 hour. The solution was filtered and added to a freeze dryer for 24 hours. The following parameters were controlled in the freeze drying process:
Freeze dryer: Telstar® LyoQuest
Temperature: −82.3° C.
Vacuum: 0.036 mbar
Chromatographic Purity: 99.25%
The solid material obtained was dried under vacuum for 15 hours at 60° C. to 65° C.
Chromatographic Purity: 99.36%

Example 4

Preparation of Pure Crystalline Form II of L-Malic Acid Salt of Sunitinib

Sunitinib (25 g), L-malic acid (8.41 g), and L-ascorbic acid (0.025 g, 0.01%) were added to de-ionized water (437.5 mL) at 35° C. to 40° C. for 1 hour. The solution was filtered and added to a freeze dryer for 48 hours. The following parameters were controlled in the freeze drying process:
Freeze dryer: Telstar® LyoQuest
Temperature: −82.3° C.
Vacuum: 0.036 mbar
Weight: 24.3 g
XRPD: As depicted in FIG. 1
Chromatographic Purity (Initial): 99.70%
Chromatographic Purity after 1M storage (at 40° C.±2° C./75%±5% RH): 99.3%
Chromatographic Purity after 1M storage (at 25° C.±2° C./60%±5% RH): 99.70%

Example 5

Preparation of Pure Crystalline Form II of L-Malic Acid Salt of Sunitinib

Sunitinib (20 g), L-malic acid (6.73 g), and L-ascorbic acid (0.1 g, 0.05%) were added to de-ionized water (350 mL) at 35° C. to 40° C. for 1 hour. The solution was filtered and charged to a freeze dryer for 24 hours. The following parameters were controlled in the freeze drying process:
Freeze dryer: Telstar® LyoQuest
Temperature: −82.3° C.
Vacuum: 0.036 mbar
Chromatographic Purity: 99.28%

The reaction mixture was further dried under vacuum at 60° C. to 65° C. for 15 hours.
Weight: 21.5 g
Chromatographic Purity: 98.51%

Example 6

Preparation of Pure Crystalline Form II of L-Malic Acid Salt of Sunitinib

Sunitinib (5 g), L-malic acid (1.08 g), and L-ascorbic acid (0.05 g, 0.1%) were added to de-ionized water (87.5 mL) at 35° C. to 40° C. for 1 hour. The solution was filtered and charged to a freeze dryer for 15 hours. The following parameters were controlled in the freeze drying process:
Freeze dryer: Telstar® LyoQuest
Temperature: −82.3° C.
Vacuum: 0.036 mbar
Weight: 4.9 g
Chromatographic Purity: 97.84%
L-Ascorbic acid content: 2.0%

Example 7

Preparation of Crystalline Form II of L-Malic Acid Salt of Sunitinib without an Anti-Oxidant Sunitinib (25 g) and L-malic acid (8.41 g) were added to de-ionized water (437.5 mL) at 35° C. to 40° C. for 1 hour. The solution was filtered and charged to a freeze dryer for 24 hours. The following parameters were controlled in the freeze drying process:
Freeze dryer: Telstar® LyoQuest
Temperature: −82.3° C.
Vacuum: 0.036 mbar
Yield: 25.1 g
Chromatographic Purity (Initial): 99.50%
Chromatographic Purity after 1M storage (at 40° C.±2° C./75%±5% RH): 87.8%
Chromatographic Purity after 1M storage (at 25° C.±2° C./60%±5% RH): 87.4%

The invention claimed is:

1. A pure crystalline Form II of an L-malic acid salt of sunitinib characterized by the data selected from the group consisting of:
   an X-Ray Powder Diffraction (XRPD) pattern substantially as depicted in FIG. 1, and a purity of at least 97.0%,
   and is chemically stable and does not degrade on storage at 25° C.±2° C. and 40° C.±2° C. at a relative humidity of 60%±5% and 75%±5%, respectively, for at least 1 month, where the pure crystalline Form II of an L-malic acid salt of sunitinib is prepared by adding an anti-oxidant to a mixture of L-malic acid and sunitinib.

2. A process for the preparation of pure crystalline Form II of an L-malic acid salt of sunitinib wherein the process comprises:
   a) adding an anti-oxidant to a mixture of L-malic acid and sunitinib; and
   b) isolating pure crystalline Form II of the L-malic acid salt of sunitinib from the mixture obtained in step a).

3. The process according to claim 2, wherein the anti-oxidant used is organic or inorganic.

4. The process according to claim 3, wherein the organic anti-oxidant used is selected from the group consisting of ascorbic acid, L-ascorbic acid, sodium ascorbate, calcium ascorbate, fatty acid esters of ascorbic acid, vitamins A and E, lipoic acid, uric acid, carotenes, glutathione, melatonin, tocopheroles, propylgallate (PG), octylgallate, dodecylgallate, tertiary butylhydroquinone (TBHQ), butylated hydroxyanisole (BHA), butylated hydroxytoluene (BHT), erythorbic acid, sodium erythorbate, 4-hexylresorcinol, polyphenols, and mixtures thereof.

5. The process according to claim 3, wherein the inorganic anti-oxidant is sodium metabisulfite.

6. The process according to claim 2, wherein the addition of the anti-oxidant to a mixture of L-malic acid and sunitinib is carried out in the presence of a solvent selected from the group consisting of water, ethers, alcohols, ketones, hydrocarbons, esters, halogenated hydrocarbons, and mixtures thereof.

7. The process according to claim 2, wherein the pure crystalline Form II of the L-malic acid salt of sunitinib is obtained from the reaction mixture by spray drying, freeze drying, agitated thin film drying, melt extrusion, solvent evaporation, desolvation, ball milling, or precipitation.

8. The process according to claim 6, wherein the addition of the anti-oxidant to a mixture of L-malic acid and sunitinib is carried out in water.

9. A process for the preparation of pure crystalline Form II of an L-malic acid salt of sunitinib, wherein the process comprises:
   a) adding sunitinib ascorbate to a mixture of L-malic acid and sunitinib; and
   b) isolating pure crystalline Form II of the L-malic acid salt of sunitinib from the reaction mixture obtained in step a).

10. A process for the preparation of pure crystalline Form II of L-malic acid salt of sunitinib, wherein the process comprises:
    a) reacting sunitinib ascorbate with L-malic acid; and
    b) isolating pure crystalline Form II of the L-malic acid salt of sunitinib from the reaction mixture thereof.

11. The pure crystalline Form II of an L-malic acid salt of sunitinib according to claim 1 substantially free of an anti-oxidant.

12. The pure crystalline Form II of the L-malic acid salt of sunitinib according to claim 11, which has an anti-oxidant content of less than 2.0%.

13. The pure crystalline Form II of an L-malic acid salt of sunitinib according to claim 1 substantially free of ascorbic acid.

14. The pure crystalline Form II of the L-malic acid salt of sunitinib according to claim 13, which has an ascorbic acid content of less than 2.0%.

15. The pure crystalline Form II of an L-malic acid salt of sunitinib according to claim 1, wherein the anti-oxidant is organic or inorganic.

16. The pure crystalline Form II of an L-malic acid salt of sunitinib according to claim 15, wherein the organic anti-oxidant is selected from the group consisting of ascorbic acid, L-ascorbic acid, sodium ascorbate, calcium ascorbate, fatty acid esters of ascorbic acid, vitamins A and E, lipoic acid, uric acid, carotenes, glutathione, melatonin, tocopheroles, propylgallate (PG), octylgallate, dodecylgallate, tertiary butylhydroquinone (TBHQ), butylated hydroxyanisole (BHA), butylated hydroxytoluene (BHT), erythorbic acid, sodium erythorbate, 4-hexylresorcinol, polyphenols, and mixtures thereof.

17. The pure crystalline Form II of an L-malic acid salt of sunitinib according to claim 15, wherein the inorganic anti-oxidant is sodium metabisulfite.

18. The pure crystalline Form II of an L-malic acid salt of sunitinib according to claim 1, wherein the step of adding the anti-oxidant to a mixture of L-malic acid and sunitinib is carried out in the presence of a solvent selected from the group consisting of water, ethers, alcohols, ketones, hydrocarbons, esters, halogenated hydrocarbons, and mixtured thereof.

19. The pure crystalline Form II of an L-malic acid salt of sunitinib according to claim 18, wherein the step of adding the anti-oxidant to a mixture of L-malic acid and sunitinib is carried out in water.

20. The pure crystalline Form II of an L-malic acid salt of sunitinib according to claim 1, wherein the pure crystalline Form II of the L-malic acid salt of sunitinib is obtained by spray drying, freeze drying, agitated thin film drying, melt extrusion, solvent evaporation, desolvation, ball milling, or precipitation.

* * * * *